(12) United States Patent
Smith et al.

(10) Patent No.: US 7,366,640 B2
(45) Date of Patent: *Apr. 29, 2008

(54) PHARMACEUTICAL WASTE IDENTIFICATION SYSTEM

(75) Inventors: Charlotte A. Smith, Wauwatosa, WI (US); James R. McCauley, Orleans, MA (US)

(73) Assignee: Pharmecology Associates, LLC, Brookfield, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/217,064

(22) Filed: Aug. 31, 2005

(65) Prior Publication Data

US 2006/0036407 A1  Feb. 16, 2006

Related U.S. Application Data

(63) Continuation-in-part of application No. 10/317,733, filed on Dec. 12, 2002, now Pat. No. 7,096,161.

(51) Int. Cl.
*G06F 11/00* (2006.01)

(52) U.S. Cl. .......................... 702/188; 702/81; 702/83

(58) Field of Classification Search ................ 702/188, 702/81, 83
See application file for complete search history.

(56) References Cited

U.S. PATENT DOCUMENTS

| | | | |
|---|---|---|---|
| 5,532,928 A | | 7/1996 | Stanczyk et al. |
| 5,662,921 A | * | 9/1997 | Fein et al. .................. 424/436 |
| 5,664,112 A | * | 9/1997 | Sturgeon et al. .............. 705/28 |
| 5,712,990 A | | 1/1998 | Henderson |
| 5,845,255 A | | 12/1998 | Mayaud |
| 5,915,240 A | * | 6/1999 | Karpf ............................ 705/2 |
| 5,958,536 A | * | 9/1999 | Gelsinger et al. .......... 428/40.1 |
| 6,097,995 A | | 8/2000 | Tipton et al. |
| 6,397,115 B1 | | 5/2002 | Basden |
| 6,542,902 B2 | | 4/2003 | Dulong et al. |
| 6,618,852 B1 | | 9/2003 | van Eikeren et al. |
| 6,633,795 B1 | | 10/2003 | Suzuki et al. |
| 2003/0004965 A1 | | 1/2003 | Farmer et al. |
| 2003/0131011 A1 | | 7/2003 | Haunschild et al. |
| 2003/0139640 A1 | | 7/2003 | Whittacre et al. |

OTHER PUBLICATIONS

Aspen Production Management for the Pharmaceutical Industry, APM, White Paper, Sep. 2001, pp. 1-21.
Holly V. Campbell, "Pharmaceuticals in the Environment: Regulatory and Nonregulatory Approaches," ERL News & Analysis, Copyright 2002 Environmental Law Institute7, Washington, D.C., Oct. 2002 (pp. 11200-11211).
"Report to Congress: Evaluating the Consensus Best Practices Developed through the Howard Hughes Medical Institute's Collaborative Hazardous Waste Management Demonstration Project and the Need for Regulatory Changes to Carry Out Project Recommendations," United States Environmental Protection Agency, Office of Solid Waste and Emergency Response, EPA530-R-02-008, Mar. 2002 (2 pgs.).

(Continued)

*Primary Examiner*—John Barlow
*Assistant Examiner*—Stephen J. Cherry
(74) *Attorney, Agent, or Firm*—Foley & Lardner LLP

(57) ABSTRACT

A pharmaceutical waste identification system presents pharmaceutical waste information and, in response to a client entering a pharmaceutical name, the system provides a pharmaceutical waste disposal recommendation. This recommendation can include a labeling recommendation for a container for the pharmaceutical, a disposal recommendation for an empty container previously containing the pharmaceutical, and a disposal recommendation for the pharmaceutical.

20 Claims, 11 Drawing Sheets

OTHER PUBLICATIONS

Memorandum of Understanding Between the U.S. Department of Health and Human Service and the U.S. Environmental Protection Agency, Sep. 30, 2002 (pp. 1-5).

Beyond RCRA: Prospects for Waste and Materials Management in the Year 2002, White Paper, Jun. 2002 (pp. 1-18).

"A Guide on Hazardous Waste Management for Florida's Pharmacies," University of Florida—Florida Center For Solid and Hazardous Waste Management (pp. 1-21).

Pharmecology Associates, LLC brochure (1 sheet).

The Pharmecology Wizard brochure (1 sheet).

Charlotte A. Smith, R.Ph, M.S., "Managing Pharmaceutical Waste—What Pharmacists Should Know," Journal of the Pharmacy Society of Wisconsin, Nov./Dec. 2002, (pp. 17-22).

Bruce R. Siecker, Ph.D., R.Ph., and Charlotte A. Smith, R.Ph., M.S., "The Long Arm of the Law in Distribution Regulatory Overview of the Drug Distribution Industry," HealthCare Distributor, Oct./Nov. 2002, (pp. 62-63).

"Improper Discard of toxic Drugs Hurts Environment, Leads to Fines," Reprinted from American Journal of Health-System Pharmacy, vol. 58, Sep. 1, 2001 (pp. 1576-1578).

Charlotte A. Smith, "Bad Medicine—Managing Drug Waste Liabilities," Reprinted from Health Facilities Management, Jan. 2001, vol. 14, No. 1 (2 pgs.).

Charlotte A. Smith, "Rationale for Inclusion of Criteria for Proper Disposal of Monograph Pharmaceutical Preparations Based on the Resource Conservation and Recovery Act," Pharmacopeial Forum, Vol. 25, No. 3, May-Jun. 1999 (pp. 8309-8312).

"Discard Woes—Hurdles Mount for Disposing of Unwanted Rx Drugs," Reprinted from Drug Topics Magazine, May 18, 1998 (1 pg.).

Claudia Morain, "EPA Still Regulates Disposal of Many Drug Materials Found in pharmacies," Reprint from Pharmacy Practice News, Jan. 1996 (1 pg.).

Charlotte A. Smith, R.Ph., M.S., "Reverse Distributors Should Establish Operational Standards," Reprinted From Wholesale Drugs, Aug. 1996 (1 pg.).

"Your Risks in Handling Outdated and Unusable Drugs—A guide to JCAHO and Regulatory Standards," Capital Returns, Inc. 1998 (pp. 1-36).

Charlotte A. Smith, R.Ph., M.S., North Memorial Health Care, "Pharmaceutical Waste Management Review," Dec. 20, 2001 (pp. 1-18).

Charlotte A. Smith, R.Ph., M.S., "Pharmaceutical Waste Management Review—Aug. 5, 2002," UWHealth, Jul. 2002 (pp. 1-138).

Charlotte A. Smith, R.Ph., M.S., "Hazardous Waste Disposal Analysis—Oct. 29, 2002," U.S. Oncology, Inc., Jul. 2002 (pp. 1-127).

Christian G. Daughton and Thomas A. Ternes, "Pharmaceuticals and Personal Care Products in the Environment: Agents of Subtle Change?," Environmental Health Perspective, vol. 107, Supplement 6, Dec. 1999 (pp. 907-938).

Dana Kolpin, Edward T. Furlong, Michael T. Meyer, E. Michael Thurman, Steven D. Zaugg, Larry B. Barber, Herbert T. Buxton, "Pharmaceuticals, Hormones, and Other Organic Wastewater Contaminants in U.S. Streams, 1999-2000: A National Reconnaissance," Environmental Science & Technology, vol. 36, No. 6, 2002 (pp. 1202-1211).

O.A.H. Jones, N. Voulvoudis and J.N. Lester, "Human Pharmaceuticals in the Aquatic Environment a Review," Environmental Technology, vol. 22 (pp. 1383-1394).

F.M. Christensen, "Pharmaceuticals in the Environment—A Human Risk?," Regulatory Toxicology and Pharmacology 28, 1998 (pp. 212-221).

Emerging Issues Conference Jun. 7-8, 2000, Minneapolis, Minnesota, http://toxics.usgs.gov/meetings/ngwa-ei.html (1 pg.).

"Pharmaceuticals and Personal Care Products (PPCPs) as Environmental Pollutants," EPA, http://www.epa.gov/nerlesd1/chemistry/pharma/index.htm (pp. 1-3).

"National Exposure Research Laboratory Environmental Sciences," EPA, http://www.epa.gov/nerlesd1/chemistry/pharma/kummer/default.htm (9 pgs.).

"Water and Health Program—Environmental Science and Engineering," Harvard School of Public Health, http://www.hsph.harvard.edu/water/ (1 pg.).

Britt E. Erickson, "Analyzing the Ignored Environmental Contaminants," Environmental Science and Technology, Apr. 1, 2002, (pp. 141A-145A).

Ovid: Bibliographic Records Sep. 30, 2002-Oct. 1, 2002 (3 pgs.).

"Widespread Pollutants with Endocrine-disrupting Effects," Our Stolen Future: Book Basics: Chemicals Implicated, http://www.ourstolenfuture.org/Basics/chemlist.htm, (pp. 1-8).

2002 Endocrine Disruptors Conferences, American Water Works Association, http://www.awwa.org/02endocrine (pp. 1-2).

"Exposure to Hazardous Drugs: Time to Reevaluate your Program," American Journal of Health-System Pharmacy, vol. 56, Jul. 15, 1999 (pp. 1402, 1427-1432).

Melissa A. McDiarmid, MD, MPH, Hubert T. Gurley, MD, and David Arrington, MS "Pharmaceuticals as Hospital hazards: Managing the Risks," Journal of Occupational Medicine, vol. 33, No. 2, Feb. 1991 (pp. 155-158).

"Cytotoxic Agents: Mechanisms of Action and Potential Toxicity," ONS Symposia, (pp. 5-8).

Page print from website http://chppm-www.apgea.army.mil/hmwp/Factsheets/MIDI-INFO.h . . . dated Dec. 12, 2005; "Military Item Disposal Instructions and Military Environmental Information Source (MIDI/MEIS) CD-ROM, Dec. 2000".

* cited by examiner

Pharmecology Associates, LLC
Providing Environmental Consultation to the Healthcare Industry

| Home | About Pharmecology | Resources | Consulting Services | CONTACT US | HELP | SITE MAP |

Welcome Phil Olson
Community Medical Center
Des Moines, IA

Example Searches

What Products Does
The Database Include

News

How Are We Doing?

FAQs

Individual Product Search | Batch Product Search | Pharmecology Admin. | Pharmecology Wizard New Search    Log Out

Search by NDC Code

NDC Code: [ ]  (Use hyphens. For example: 1234-456-10)

Search by Product Name

Product name: [ ]    Strength (optional): [ ]

Search by Generic Name or Active Ingredient

Generic name: [ ]    Manufacturer (optional): [ ]    Strength (optional): [ ]

Search

*Hints
1. Enter full or partial names
2. Enter the beginning of the strength, ignoring the concentration or additional ingredients

FIG. 7

Pharmecology Associates, LLC
Providing Environmental Consultation to the Healthcare Industry

| Home | About Pharmecology | Resources | Consulting Services | CONTACT US | HELP | SITE MAP |

Pharmecology Wizard

Welcome Phil Olson
Community Medical Center
Des Moines, IA

HAZARDOUS POTENTIAL KEY
- Federal
  - Hazardous Waste
- State
  - Hazardous Waste
  - Risk Management Hazardous Waste
  - Not Hazardous How Does the Detail Search Logic Work?

Is Your Product Missing?

State Regulatory Alerts

Individual Product Result   Additional Information

Federal Hazardous Waste        New Search    Log Out

Product: 0002-2576-05 Paragoric Liquid        473 mls Rx
Generic: Paragoric
Manufacturer: Lilly                           DEA: Schedule CIII

Recommended Waste Classification

Regulated as federal hazardous waste:
D001-Ignitable

Recommended Waste Stream

Manage as hazardous waste:
Ignitable

Highlights

FIG. 8

Pharmecology Associates, LLC
Providing Environmental Consultation to the Healthcare Industry

| Home | About Pharmecology | Resources | Consulting Services | CONTACT US | HELP | SITE MAP |
|------|---|---|---|---|---|---|
| | | | | | | Pharmecology Wizard |

Welcome Phil Olson
Community Medical Center
Des Moines, IA

Additional Information | Individual Product Result
Federal Hazardous Waste (New Search)  (Log Out)

Barium Sulfate

Par Merck Index Twelfth Edition:
BArium Sulfate (BaSO$_4$) mal.wl. 233.39:

BA 58.84%    S 13.74%    O 27.42%

Preparations of barium sulfate for radiographic examination of the GI tract come in varying concentrations, the lowest being 1.2% (Readi-CAT Suspension by E-Z-EM):

$1.2\% = \frac{1.2gm}{100ml} = \frac{12grr}{1000ml}$

Since barium is 58.84% of barium sulfate, 12gm x 5884 = 7.06gm of barium $\frac{7.06gm}{1000ml} = \frac{7060mg}{1L}$ The RCRA D list regulatory limit for barium is 100mg/L, therefore even dilute solutions of barium sulfate exceed the toxicity characteristics for barium

HAZARDOUS POTENTIAL KEY
- Federal Hazardous Waste
- State Hazardous Waste
- Risk Management Hazardous Waste
- Not Hazardous How Does the Detail Search Logic Work?

Is Your Product Missing?

State Regulatory Alerts

FIG. 9

| Internal Key | NDC | ReportLabelName | Waste Classification | Waste Stream | EPA_Code1 | Reason | Seq |
|---|---|---|---|---|---|---|---|
| 100 | 2323433 | SYMBYAX CAP 12-50MG | Not regulated as federal hazardous waste | Non-Hazardous | | Non-Hazardous | 1 |
| 200 | 2951501 | HUMULIN INJ 50/50 | Regulated as federal hazardous waste | Toxic | D024 - m-Cresol | M-CRESOL | 2 |
| 300 | 4026549 | DEMADEX TAB 100MG | Not regulated as federal hazardous waste | Non-Hazardous | | Non-Hazardous | 3 |
| 400 | 5460923 | PROPYLTHIOUR TAB 50MG | PharmE Hazardous waste | Toxic | | Report on Carcinogens(11th) - Expected Carcinogens | 4 |
| 9500 | 65473070001 | URECHOLINE TAB 50MG | Not regulated as federal hazardous waste | Non-Hazardous | | Non-Hazardous | 95 |
| 9600 | 66860002102 | EPINEPHRINE INJ 1MG/ML | Regulated as federal hazardous waste | Toxic | P042 - Epinephrine | EPINEPHRINE | 96 |
| 9700 | 99207001551 | LOPROX CRE 0.77% | Not regulated as federal hazardous waste | Non-Hazardous | | Non-Hazardous | 97 |
| 9800 | 5460923 | PHISOHEX LIQ 3% | Regulated as federal hazardous waste | Toxic | U132 – Hexachlorophene | HEXACHLOROPHENE | 98 |

FIG. 11

PHARMACEUTICAL WASTE IDENTIFICATION SYSTEM

CROSS REFERENCE TO RELATED APPLICATIONS

The present application is a continuation-in-part application of U.S. application Ser. No. 10/317,733 entitled "Pharmaceutical Hazardous Waste Identification and Management System" filed on Dec. 12, 2002 and assigned to the same assignee as the present application.

FIELD OF THE INVENTION

The present invention relates generally to asset management systems. More particularly, an exemplary embodiment of the present invention relates to a pharmaceutical hazardous waste identification and management system.

BACKGROUND OF THE INVENTION

Pharmaceuticals are chemicals, often hazardous, which have not in the past received the attention given to other hazardous chemicals with respect to their impact on either employee safety during transport preparation and administration or their impact on human health and the environment when discarded. Recent studies in the US and Europe have demonstrated the presence of common pharmaceuticals in waste waters, surface waters, and drinking waters, focusing attention on their disposition as waste. Other studies on a category of chemicals known as endocrine disruptors have demonstrated that these chemicals, which include some pharmaceuticals, can have a devastating and irreversible effect on the human fetus and new born, causing gender related dysfunction, including cancers, and neurological damage.

The Resource Conservation and Recovery Act, RCRA, was enacted in 1976 to regulate the disposal of solid and hazardous waste in the United States and is enforced by the Environmental Protection Agency (EPA). The RCRA criteria of hazardous waste apply to waste pharmaceuticals in addition to other chemicals. It is very difficult to apply these criteria to finished dosage forms, such as tablets, capsules, liquids and injectables because the regulation was written for bulk chemicals. In addition, healthcare personnel, including pharmacists and nurses, have not received training on RCRA in their professional curricula and are unaware of the regulation and need to comply. Due to both ignorance of the regulation and the difficulty in complying, many waste pharmaceuticals are being disposed through sewering, landfilling, or inadequate incineration in violation of RCRA.

No commercially available system exists at this time to assist healthcare organizations, pharmacies, drug wholesalers, manufacturers or other interested parties in determining if the pharmaceutical products they are discarding meet the definition of hazardous waste under RCRA. In addition, no system exists at this time to assist researchers in the areas of occurrence, concentrations, and ecotoxicologic data for waste pharmaceuticals in the environment. Finally, no existing system defines which pharmaceuticals are considered hazardous materials under OSHA (Occupational Safety and Health Administration) regulations with respect to employee safety in their handling, preparation and administration.

Thus, there is a need for a system and method for identification and management of pharmaceutical hazardous waste. Further, there is a need for a system that aids health care providers, researchers, and others in handling, preparing, and administering pharmaceutical products. Even further, there is a need to accurately provide safe disposal procedures for pharmaceutical hazardous waste.

SUMMARY OF THE INVENTION

A pharmaceutical waste identification system presents pharmaceutical waste information and, in response to a client entering a pharmaceutical name, the system provides a pharmaceutical waste disposal recommendation. This recommendation can include a labeling recommendation for a container for the pharmaceutical, a disposal recommendation for an empty container previously containing the pharmaceutical, and a disposal recommendation for the pharmaceutical.

An exemplary embodiment is related to a pharmaceutical waste identification system that integrates disparate information regarding pharmaceuticals to provide an indication of which pharmaceuticals are hazardous wastes as defined by respective national, international and state regulations and/or which are hazardous materials as defined by the US OSHA regulations. A subset of this information offers a global repository with respect to the occurrence, concentrations, and ecotoxicologic data of pharmaceuticals based on peer reviewed data provided by environmental toxicologists and related scientists.

Another exemplary embodiment is related to a pharmaceutical waste identification and management computer-implemented method for providing an indication of pharmaceuticals that are hazardous wastes as defined by regulations. The method comprises gathering pharmaceutical waste information associated with a pharmaceutical, storing the gathered pharmaceutical waste information into a database, and providing access to the information associated with the pharmaceutical waste information to a client.

Another exemplary embodiment is related to a method of enabling access to pharmaceutical waste information over a network. The method comprises using a first processing system to maintain a pharmaceutical waste information processing unit, receiving a signal for invoking the pharmaceutical waste information processing unit from a remote processing system via a network, and using the first processing system to operate the pharmaceutical waste information processing unit in response to the signal. The pharmaceutical waste processing unit receives and processes requests for pharmaceutical waste information associated with a number of pharmaceuticals. The signal for invoking the pharmaceutical waste information processing unit is transmitted from the remote processing system in response to a selection of a hypermedia link.

Another exemplary embodiment includes a method of enabling access to pharmaceutical waste information over a network in a local processing system. The method includes receiving a request from a first remote processing system via a network and, in response to receiving the request, transmitting to the first remote processing system over the network information for enabling the first remote processing system to output a pharmaceutical waste information interface to a user. This is generated by the first remote processing system according to a hypermedia link provided to the first remote processing system from a separate processing system on the network. The pharmaceutical waste information interface includes pharmaceutical waste information for a number of pharmaceuticals. The pharmaceutical waste information interface is configured to enable the user to request specific pharmaceutical waste information for a pharmaceutical.

Another exemplary embodiment is related to a processing system comprising a central processing unit (CPU) and a storage device coupled to a processor and having stored there information for configuring the CPU to maintain a pharmaceutical waste information processing unit corresponding to a client, receive a request for invoking the pharmaceutical waste information processing unit from a remote processing system via a network, and operate the pharmaceutical waste information processing unit in response to the request. The pharmaceutical waste information processing unit is configured to provide a user interface for enabling the client to submit requests for information on pharmaceutical waste information of the pharmaceuticals and configured to receive and process the requests. The request is transmitted from the remote processing system in response to a selection of a hypertext link by the user.

Another exemplary embodiment is related to an apparatus for enabling access to pharmaceutical waste information from a plurality of unrelated institutions over a network. The apparatus comprises means for receiving a signal from a remote processing system via the network and means for invoking a pharmaceutical waste information processing unit in a local processing system in response to the signal. The signal is transmitted from the remote processing system in response to a selection of a hypermedia link by a client, where the hypermedia link is provided by a web site of an institution. The means for invoking includes providing information for generating a user interface for access to pharmaceutical waste information. The pharmaceutical waste information processing unit is configured to receive and process requests for pharmaceutical waste information.

Other principle features and advantages of the invention will become apparent to those skilled in the art upon review of the following drawings, the detailed description, and the appended claims.

BRIEF DESCRIPTION OF THE DRAWINGS

The exemplary embodiments will hereafter be described with reference to the accompanying drawings, wherein like numerals denote like elements, and:

FIGS. 7, 8, and 9 are displays depicting exemplary user interfaces utilized in the pharmaceutical hazardous waste manager of FIG. 1 in accordance with exemplary embodiment;

FIG. 11 is a chart detailing formulary analysis results in accordance with an exemplary embodiment.

DETAILED DESCRIPTION OF EXEMPLARY EMBODIMENTS

A system for and method of identifying and managing pharmaceutical hazardous waste are described. In the following description, for purposes of explanation, numerous specific details are set forth in order to provide a thorough understanding of the present invention. It will be evident, however, to one skilled in the art that the exemplary embodiments may be practiced without these specific details. In other instances, structures and devices are shown in block diagram form in order to facilitate description of the exemplary embodiments.

In one embodiment, a computer system is used which has a central processing unit (CPU) that executes sequences of instructions contained in a memory. More specifically, execution of the sequences of instructions causes the CPU to perform steps, which are described below. The instructions may be loaded into a random access memory (RAM) for execution by the CPU from a read-only memory (ROM), a mass storage device, or some other persistent storage. In other embodiments, hardwired circuitry may be used in place of, or in combination with, software instructions to implement the functions described. Thus, the embodiments described herein are not limited to any specific combination of hardware circuitry and software, nor to any particular source for the instructions executed by the computer system.

Figure 1:
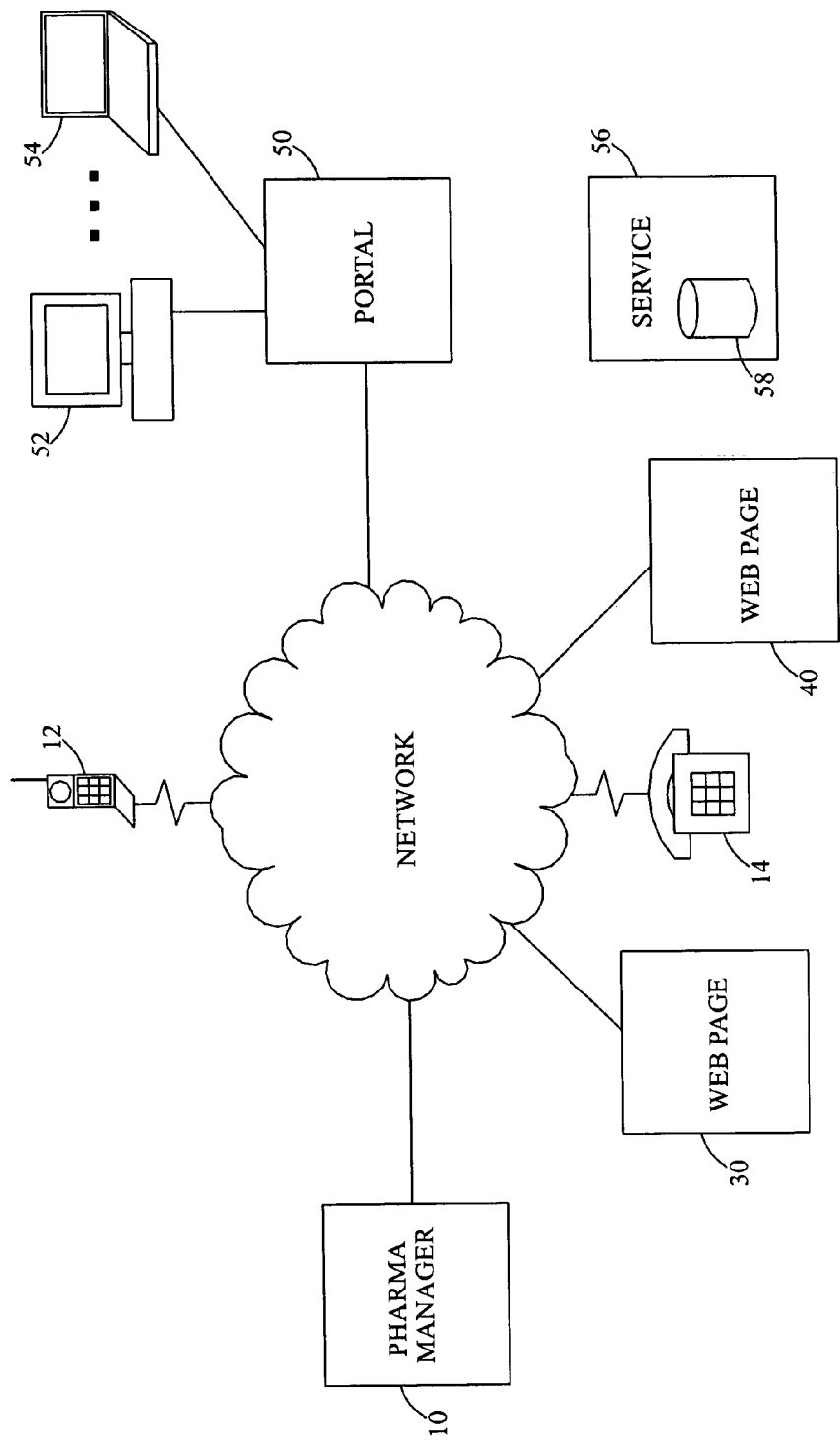
FIG. 1 is a general diagrammatical representation of a pharmaceutical waste manager connected to a communications network.

FIG. 1 illustrates an exemplary pharmaceutical waste identification and management system. This system can include a connection between a pharmaceutical waste manager 10 and a network 20. Pharmaceutical waste manager 10 provides access to pharmaceutical hazardous waste information available locally and via network 20. In an exemplary embodiment, network 20 is the Internet, a worldwide network of computer networks that use various protocols to facilitate data transmission and exchange. Network 20 can use a protocol, such as, the TCP/IP network protocol or the DECnet, X.25, and UDP protocols. In alternative embodiments, network 20 is any type of network, such as, a virtual private network (VPN), an Ethernet, or a Netware network.

Network 20 can include a configuration, such as, a wide area network (WAN) or a local area network (LAN). Network 20 preferably provides communication with Hypertext Markup Language (HTML) Web pages 30 and 40. Web pages can also include XML, Extensible Markup Language. Web pages 30 and 40 include a variety of data on a variety of Web servers. Network 20 also provides communication with a communication network portal 50 which couples computers 52 and 54 and a service 56 including a database 58 to network 20. Service 56 is any type of company, content or service provider with a connection to network 20. Database 58 is a storage medium for data and may be an optical, magnetic, or any other suitable storage medium.

Generally, pharmaceutical waste manager 10 can be implemented using a computer server configured by software. Preferably, the server includes read/write memory, such as, disc drives and other storage. A customer or client can access pharmaceutical waste manager 10 via a web page 30 or 40 which is conveyed to the client at computer 52 or 54. Computers 52 or 54 can be any type of computing device, including work stations, laptops, notebooks, personal digital assistants (PDAs), cell phones, beepers, or other equipment capable of communication with network 20. In another embodiment, pharmaceutical waste manager 10 can be accessed via telephones, such as, a cell phone 12 or a standard telephone 14. Other user interface platforms may also be provided for using pharmaceutical waste manager 10. Such user interface platforms include, for example, WAP (wireless application protocol) and web interfaces.

According to an exemplary embodiment, pharmaceutical waste manager 10 implements a process by which waste pharmaceuticals or formulations are designated as either federal, state, or non-RCRA management hazardous waste (recommended for RCRA incineration) when discarded. Non-RCRA hazardous waste includes:

Formulations containing more than one P or U listed drug;
The National Institute of Occupational Safety and health (NIOSH) Hazardous Drug Alert Appendix A;
The Occupational Safety and Health Administration (OSHA) Technical Manual Section 6, Chapter 2, Appendix VI:2-I;
The U.S. Department of Health and Human Services National Toxicology Program's Report on Carcinogens ($11_{th}$ Edition);
Chemotherapy agents not already listed as RCRA hazardous;
Additional drugs meeting OSHA or NIOSH criteria;
Drugs with LD50s at or below 50 mg/kg;
Endocrine disruptors;
Bulk powders;
Vitamin or mineral preparations that may fail the toxicity characteristic due to chromium, selenium, or cadmium for which there is inadequate data at this time;
Biohazardous (Infectious) category for live attenuated vaccines, blood products, globulins, and other pharmaceuticals requiring disposal as infectious waste.

For example, the active and inactive ingredients can be compared by pharmaceutical waste manager 10 with criteria presented in the United States' Resource Conservation and Recovery Act (RCRA) definitions of federal hazardous waste. In general, RCRA definitions include a P list, a U list, and four characteristics of hazardous waste: ignitability, corrosivity, toxicity, and reactivity.

Pharmaceutical waste manager 10 can account for any of a variety of different state criteria. The Environmental Protection Agency (EPA) authorizes all states in the United States except Iowa and Alaska to manage their own environmental regulatory and enforcement programs and have regulations similar to federal regulations. States such as Minnesota and Washington have additional categories, such as Minnesota's "lethal hazardous waste" and Washington's "dangerous hazardous waste" criteria.

Pharmaceutical waste manager 10 can also account for newer drugs not formally categorized by regulations. Federal regulations have not been updated substantially since 1976 and have not evaluated new drugs for toxicity with respect to their environmental hazardous. Therefore, many drugs released since 1976, including hundreds of chemotherapy agents, do not come under RCRA regulation and, technically, can be lawfully discarded in the sewer system or landfills, posing a potential risk to human health and the environment. Pharmaceutical waste manager 10 can identify these agents and recommend treatment as hazardous waste when discarded.

Pharmaceutical waste manager 10 can evaluate each drug formulation having a unique National Drug Code (NDC) identifier and classify the drug as either federally hazardous, potentially state hazardous (individual drugs will be evaluated in the next iteration), risk management hazardous or nonhazardous. In an exemplary embodiment, non-hazardous is further differentiated into non-hazardous sewerable, non-hazardous municipal solid waste, and potentially non-hazardous pharmaceutical (recommended for non-RCRA incineration). Other unique identifiers can be used where a NDC identifier may or may not exist, as in the case of laboratory chemicals.

Advantageously, pharmaceutical waste manager 10 provides information heretofore unavailable. Pharmaceutical reverse distributors such as Capital Returns, Inc., (CRI) of Milwaukee, Wis., have categorized drugs which have physically entered a warehouse as to their federal status. Some attempt has been made to identify items such as chemotherapy agents and to discard them as hazardous waste, but they are not delineated as "risk management" in the resulting waste categorization. In other words, they are identified as federal hazardous waste even though they do not actually designate as such under the RCRA criteria. It is important for a waste generator to consciously make the risk decision to include these items as hazardous waste due to higher management and disposal costs. There are no state differentiators. The universe of current drug formulations currently categorized by CRI comprises about 40% of drugs available on the marketplace today.

In an exemplary embodiment, pharmaceutical waste manager 10 uses a unique coding system of red for regulated hazardous waste, yellow for risk management hazardous waste, and green for nonhazardous waste. In alternative embodiments, colors such as red/orange/yellow/green are used to distinguish other differentiations, such as between types of non-hazardous waste.

In another exemplary embodiment, pharmaceutical waste manager 10 indicates the P, U or D code (characteristic waste) of the federally regulated item and presents a recommended waste stream. The waste streams can be categorized as toxic, ignitable, corrosive acid, corrosive base and reactive. The toxic waste stream, for example, may involve both P, U and those D wastes which exhibit the characteristic of toxicity.

Pharmaceutical waste manager 10 can present to a user a detailed reasoning behind the hazardous waste decision, including calculations to justify the decision, as in the case of trace heavy metals such as barium, cadmium, chromium, selenium, silver, and preservatives such as m-cresol, thimerosal, and phenylmercuric acetate.

In at least one exemplary embodiment, pharmaceutical waste manager 10 includes a subscription search capability that enables a site administrator at a single physical location to assign an unlimited number of password protected user identifiers to key personnel within a facility. These individuals, from departments such as pharmacy, nursing, infection control, environmental services and safety, can then access the specific product information at any time to determine how to discard a particular pharmaceutical. This information can be used for routine discards as well as for spills and breakage. Knowledge of the hazardous nature of a spill enables personnel to comply not only with state and federal regulations regarding disposal but also with the facility's internal hazardous material management plan. Further, manager 10 creates an audit trail of all inquiries to allow facilities to demonstrate compliance with regulations and any internal hazardous material management plan.

Advantageously, pharmaceutical waste manager 10 provides an integration of pharmaceutical industry references (e.g., Medi-Span), proprietary data (e.g., Capital Returns), pharmaceutical manufacturer web-based information, U.S. EPA regulations, state environmental protection regulations, and OSHA and ASHP (American Society of Health-System Pharmacists) criteria for hazardous drugs into a web-based database searchable by National Drug Code (NDC), trade name, generic name, or ingredient.

Advantageously, pharmaceutical waste manager 10 enables subscribers to determine if a drug product is: (1) a hazardous waste based on federal EPA regulations; (2) a hazardous waste based on state environmental protection agency regulations; (3) recommended to be treated as hazardous waste even though not falling under federal or state regulations; and/or (4) an OSHA hazardous material based on OSHA and industry criteria. Further, information on how to dispose of empty primary containers for hazardous and chemical drugs can be provided. Yet still further, labeling instructions for primary containers of drugs of various hazard classes can be selectively provided. Primary containers can include vials, ampules, IV bags, syringes, or other containers used to hold a drug prior to its use. In an exemplary embodiment, the labeling can include Department of Transportation (DOT) guidance for RCRA containers.

Pharmaceutical waste manager 10 can be customized to individual organizations to include drug formulary analysis, custom waste stream designation, and hazardous waste accumulation data for waste generator status determination. Further, pharmaceutical waste manager 10 can include an integrated waste stream designation process involving new waste containers and labeling. According to an exemplary embodiment, pharmaceutical formulary analysis involves either an electronic transfer of the hospital's formulary with the required data fields or a request by the client to the drug wholesaler for 12 months of purchasing history for pharmaceuticals. This information is presented in a Microsoft Excel or Access or other type of spreadsheet. The data preferably includes the following fields: NDC, brand name, generic name, manufacturer, strength, dosage form, and package size. This information is preferably electronically communicated to the pharmaceutical waste manager 10 and the data is compared to data in the system. Appropriate waste streams, waste codes, reason codes, and corresponding identifiers are applied to the data. When incoming data is not found by the manager 10, manual evaluation is conducted. When incoming National Drug Codes are not accurate, research is conducted to determine the correct code and the codes are edited. The completed spreadsheet can include the following pages: Summary, Brief Wizard Results, Full Wizard Results, Percent, Products, Field Descriptions, Report Group Crosstab.

Advantageously, pharmaceutical waste manager 10 can include hazardous waste definitions and criteria of other countries or government entities, such as the European Union. Moreover, pharmaceutical waste manager 10 provides a web-based searchable database to enable scientists in the areas of environmental toxicology and related fields to share peer-reviewed data regarding the occurrence, concentrations, and ecotoxicologic data for specific pharmaceuticals in the environment in one global repository.

In another embodiment, pharmaceutical waste manager 10 includes a custom application whereby waste designation information is imbedded in a drug wholesaler's system and flags those items that become hazardous waste so the pharmacy can tag them with an appropriate label. Currently, drug distributors routinely affix master bar codes on shipping totes which contain a list of all items in the tote. These are delivered daily to pharmacies and healthcare facilities. The barcode is then scanned and a list of the items appears on the terminal to facilitate check in of the products. The ability to tag pharmaceuticals with a hazardous waste designation can assist proper waste segregation if and when the pharmaceutical is discarded for any reason.

In another embodiment, pharmaceutical waste manager 10 includes a custom application whereby waste designation information is imbedded in a hospital or healthcare system's dispensing software and flags items that become hazardous waste so they can be tagged with an appropriate label so that personnel can dispose of waste pharmaceuticals appropriately.

In another embodiment, pharmaceutical waste manager 10 includes a custom application whereby waste designation information is imbedded in a hospital or healthcare system's automated dispensing software and flags those items that become hazardous waste so personnel can dispose of waste pharmaceuticals appropriately.

In another embodiment, pharmaceutical waste manager 10 includes a custom application whereby waste designation information is imbedded into master data files generated and sold to the pharmaceutical industry by medical data companies such as Medispan and First Data Bank and automatically flags those items that become hazardous waste so healthcare facilities, wholesalers, and manufacturers can dispose of waste pharmaceuticals appropriately.

In another embodiment, pharmaceutical waste manager 10 includes a custom application whereby waste designation information is manually applied or electronically imbedded in a hospital or healthcare system's unit dose packaging machine and results in either an appropriately colored packaging or colored identifying mark being generated so that personnel can dispose of waste pharmaceuticals appropriately.

In another embodiment, pharmaceutical waste manager 10 includes a custom application whereby waste designation information is electronically imbedded in the packaging software of a machine used to package medication for dispensing by a high volume robotic dispensing machine, generating an appropriately marked label so that personnel can dispose of the waste pharmaceuticals appropriately.

In another embodiment, pharmaceutical waste manager 10 is utilized by federal, state, county, and city regulatory agencies, including wastewater treatment plants, to determine the manner in which specific waste pharmaceuticals should be disposed: RCRA treatment, storage and disposal facility; regulated medical waste incinerator; municipal incinerator; landfill; sewer system.

Another feature of pharmaceutical waste manager 10 is the ability to track wastes by weight by month, thereby insuring that the EPA is notified of the correct generator status and providing an audit trail to justify that decision. Hazardous waste generators are required to track the weight of hazardous waste generated monthly. There are three categories of generators recognized by the EPA: large quantity (full regulation), small quantity, and conditionally exempt small quantity. Certain limits apply to the last two categories; for example, if more than 1 kg. of combined P-listed wastes are generated in a calendar month, the generator comes under full regulation as a large quantity generator for that month. Additional categories, such as healthcare laboratory chemicals, can be included as well.

Pharmaceutical waste manager 10 can also incorporate OSHA hazardous materials information and make such information available. Currently, OSHA requires all non-drug products to carry appropriate warning labels if they are considered hazardous materials by the manufacturer. Because FDA has jurisdiction over drug labeling, and has not mandated such information on drug packaging, entities in all phases of the drug distribution system have great difficulty in determining which drugs are considered hazardous materials under OSHA and in obtaining the required Material Safety Data Sheets. It is the manufacturers' responsibility to make the hazard determination based on their knowledge of the properties of the drug product.

According to an exemplary embodiment, specific drug product results are linked to a supporting Material Safety Data Sheet (MSDS). Manufacturers in all industries in the U.S. are required by OSHA to generate an MSDS for all products they deem to be hazardous materials under the OSHA definitions and to pass this information on to their distributors and customers. The MSDS includes a variety of required information, such as the chemical and common name, physical and chemical characteristics, physical hazards, health hazardous, primary route of entry, permissible exposure limits, emergency and first aid procedures, spill clean up information, etc. MSDSs for drug products are somewhat problematic to obtain, since most MSDSs are for raw chemicals. Providing such a link to a manufacturers' website enhances pharmaceutical waste manager 10. Requirements for MSDSs under the OSHA Hazard Communication Standard can be found on the Internet at http://www.osha.gov/pls/oshaweb/owadisp.show document?p table=STAND ARDS&p id=10099#1910.1200(g).

Pharmaceutical waste manager 10 can also provide EPA disposal information or OSHA hazardous materials information to the pharmaceutical industry when such information is added to labeling requirements either voluntarily or by regulatory or congressional mandate. Currently, drug labeling is controlled by FDA and there are no requirements to label drug packages with either EPA disposal information or OSHA hazardous materials information.

Pharmaceutical waste manager 10 can provide information regarding which laboratory chemicals become hazardous waste when discarded. Heretofore, there has not existed a database or system to identify which hospital and clinic laboratory chemicals become hazardous waste. Manager 10 can be expanded to teaching and research laboratories within academic centers, such as colleges and universities.

Pharmaceutical waste manager 10 can provide information to academic centers, including schools of pharmacy, to assist pharmacy students in understanding and applying regulatory and best management practices of pharmaceutical waste management in lecture and laboratory practice settings.

Pharmaceutical waste manager 10 can provide information to assist physicians in determining the relative environmental hazards of pharmaceuticals. In an exemplary embodiment, a physician or other care provider can have on a PDA (Personal Digital Assistant) display relative hazardous waste information for therapeutically equivalent products to encourage the physician to prescribe the least environmentally damaging pharmaceutical.

Pharmaceutical waste manager 10 can identify pharmaceuticals based on drug entities and their chemical abstract numbers which may or may not serve a common identifier, rather than the NDC code. Advantageously, any common identifier can be supported by pharmaceutical waste manager 10. As such, pharmaceutical waste manager 10 can provide a single repository for disparate research. State and federal environmental agencies and academic centers around the world have identified pharmaceuticals and personal care products as emerging water contaminants and as endocrine disruptors (those chemicals that mimic or disrupt naturally occurring hormones, especially during fetal development).

By way of example, pharmaceutical waste manger 10 can include a process for bringing together several proprietary databases to enable multiple analysts to review each item. Manager 10 can also enable a quality assurance approval of each decision by a second analyst. This process can include the following operations.

Pharmaceutical waste manager 10 accesses a commercial database for which manager 10 has a subscription. An example of such a commercial database is the Facts and Comparisons' Medispan database. Manager 10 uses the commercial database as a source for basic identifying information about currently used pharmaceutical products, identified by NDC code.

In an exemplary embodiment, the entire commercial database is initially loaded and all products are marked with a "Requires Initial Review" status. Manager 10 periodically receives updates from the commercial database and loads that information into the database. Any new products are marked with a "Requires Initial Review" status; any products with significant changes are marked with a "Requires Follow-up Review" status. While current pharmaceuticals should be in the commercial database, if a product is not in the database, it can be added manually.

Pharmaceutical waste manager 10 relies on the commercial database for basic information about each product, including, but not limited to NDC code, product name, generic name, brand or trade name, active and inactive ingredients, package size, strength, form, manufacturer, and a product category coding system.

The database and supporting processes include provisions to capture information about the waste characteristics for each product. This includes attributes to indicate if a product is federally hazardous, risk management hazardous, or non-hazardous. It also includes supporting flags and references to the EPA codes to indicate why a product is hazardous. Additional attributes are available to indicate if a product is considered hazardous by OSHA, and why. The waste categorization can be supported by multiple reason codes, additional descriptions, the relevant source to backup the decision, the page number within the source, an audit trail of changes, and additional comments.

All waste characteristic information can be captured based on country, such as the United States, or region, such as the European Union. Additional criteria can also be captured at a state or province level within a country.

After the initial commercial database is loaded, the system electronically matches it with historical product categorization from an existing proprietary database. An example of such an existing proprietary database is a database available from Capital Returns, Inc. of Milwaukee, Wis.

The database constructed by Capital Returns, Inc. was built inductively, item by item, as specific items were received at the facility. Each item was reviewed manually by a person skilled in the art of making hazardous waste determination decisions. No differentiation was made between an item that was technically hazardous waste under RCRA and an item, such as an unlisted chemotherapy drug, which was not technically RCRA hazardous waste but should be treated as such under conservative risk management practices.

In contrast, pharmaceutical waste manager 10 makes distinctions with drugs that do not technically fall under a RCRA hazardous waste category but could be considered hazardous using a risk management category. The database utilized with the pharmaceutical waste manager 10 was developed deductively, starting with the entire universe of drugs available to the U.S. market, grouping them by class, noting the ingredients which could potentially cause them to become hazardous waste, and applying knowledge of the RCRA regulations to these classes of drugs.

The database constructed represents a small subset of not only the total universe of drug products but also represents only one piece of the process used to develop the pharmaceutical waste manager 10. The Capital Returns database includes no consolidated review platform accessible by multiple reviewers, no tracking of reviewer decisions and notes, no consistent reason codes with defined explanatory texts, no state specific regulatory guidance, no class groupings and no electronic audit trail of reviews and approvals.

Pharmaceutical waste manager 10 includes a database with a common reference file containing the thousands of ingredients, both active and inactive, used in manufacturing pharmaceutical products. These ingredients are reviewed and those which may make a particular product hazardous are identified. For example, alcohol may cause a product to become ignitable; barium may cause a product to be considered toxic.

Identifying hazardous pharmaceuticals presents unique problems not found in bulk chemicals. The formulation of bulk chemicals into finished pharmaceutical dosage forms is a highly technical and precise process which involves not only precise dosing but also the appropriate solvents, excipients, diluents, fillers, preservatives, coatings, etc. While the primary purpose is accurate and appropriate drug delivery, these formulations compound the difficulty inherent in determining if a specific drug product meets the criteria of a hazardous waste when discarded. Pharmaceutical waste manager 10 identifies all potential ingredients of a finished dosage that could cause the item to become a hazardous waste when discarded, such as alcohol content, heavy metal content, and preservative content, in addition to the active ingredients. In so doing, pharmaceutical waste manager 10 takes into account all aspects of these very specific and consistently defined criteria. Pharmaceutical waste manager 10 also applies to all FDA licensed drugs available in the United States of America, which are themselves identified by a unique National Drug Code.

By way of example, pharmaceutical waste manager 10 can identify disposal hazards of commonly prepared intravenous (IV) solutions to note how such compounding may change the waste category. For example, paclitaxel, a common chemotherapy drug, contains over 49% alcohol when it is in its original formulation, making it an ignitable hazardous waste if disposed. When diluted, however, it no longer exhibits ignitability but should be disposed as hazardous waste due to its toxicity. A number of other drugs change their waste disposition when diluted, while others, such as P and U listed chemicals, do not.

In an additional embodiment, the results for a particular product search include a link to relevant Policies and Procedures pertaining to disposal of that drug product within that facility. Yet another embodiment includes the use of benchmarking databases with pharmaceutical waste manager 10 in which data derived from the review of the hospital's formulary is coupled with additional demographic data such as the number of licensed bed, average daily census, and type of hospital (i.e. Level Two Trauma Center). This data is tied to specific information regarding hazardous pharmaceutical waste management, such as average cost per patient day, usage of waste containers (size, number, number per nursing unit/month), cost per pound per waste stream, etc., implementation model used, and other relevant data not now currently available in the marketplace.

The database of manager 10 can include a sophisticated reason coding technique to facilitate the review and waste categorization for each product. For example, one reason code may apply to RCRA federally hazardous chemotherapy waste; another may apply to other chemotherapy products we consider risk management hazardous.

In an exemplary embodiment, the database relies upon the product category coding system of the commercial database. Each category is reviewed to determine if products in a particular category are never hazardous, rarely hazardous, or frequently hazardous.

Within the database, each product category is assigned to a particular analyst for review. The database also includes additional attributes to track the status of each product, including, but not limited to, who initially reviewed a product and when, who initially approved a product's waste characteristics and when, who performed a follow-up review or approval, the product's current status, and information to highlight products which require particular care in reviewing.

Pharmaceutical waste manager 10 presents products assigned to each analyst for his or her review, using a distributed copy of the database. In addition, analysts and management can look at any product to review its current characterization. In an exemplary embodiment, pharmaceutical waste manager 10 includes a dynamic workflow management and tracking system to identify the current status of the entire database, each product category, sub-category, drug, or particular product. The tracking system identifies products requiring review, requiring approval, and those where our analysis is complete.

Pharmaceutical waste manager 10 groups together products by category, sub-category, and drug to highlight differences and similarities between particular products within a drug or within a particular category or sub-category. As a result, if a manufacturer issues a particular drug in a new formulation (e.g., a new NDC number), the analyst can compare it to other products for that drug to determine if the new drug shares the waste characteristics of the products which have already been reviewed.

Based upon the product category assignments, a particular analyst reviews products by category, sub-category, and particular drug. Within a drug, the analyst can review each specific NDC code to review its current detail information, particular ingredients, form, and existing characteristics. Based upon his or her expertise, an analyst can select a group of products (using, for example, NDC codes) within a particular drug and analyze them together.

For each specific product or group of products within a particular drug, the analyst can evaluate its potential to become hazardous waste. To perform this analysis, the analyst uses both proprietary and publicly available industry reference material. This includes, but is not limited to, federal and state regulations, industry subscription databases, manufacturer specifications, and similar information. In some cases, the analyst accesses this information over the Internet; in other cases, the analyst will refer to published texts and similar documents.

The analyst determines the waste characteristics for each product or group of products within a particular drug. In addition to the specific determination if a product is non-hazardous, federally hazardous, risk management hazardous, or state hazardous, the analyst indicates the waste stream, and specifies other attributes such as the reason code, the EPA code, and OSHA characteristics. The analyst documents the information which supports the determination and includes any particular comments to explain the determination.

If an analyst has questions about a particular product or set of products, he or she can forward those products to another analyst for review. When an analyst forwards products for review, he or she indicates why those products require more detailed analysis. After the analysts review each product or group of products another analyst reviews those determinations and approves the decisions. For some products, the determination can be very technical and detailed. Each reviewing analyst and each approving analyst can flag a particular product or group of products as particularly noteworthy. Pharmaceutical waste manager 10 allows other analysts or management to look at only these products for an additional check.

Pharmaceutical waste manager 10 can be reconfigured for an additional set of clients, drug manufacturers, who in the future may need to examine the environmental impact of new drugs in compliance with FDA requirements. Currently, the FDA exempts new drugs from going through a National Environmental Policy Act (NEPA)-required environmental impact statement (EIS) if they are expected to enter water systems at a concentration of less than one part per billion. This evaluation is calculated using a relatively simple formula based on total production per year. Concerns are being raised that this naive approach ignores the total aquatic impact of drugs with similar mechanisms of action. New regulations may require comparative and cumulative data which could be made available through the database as it matures.

In their day-to-day working with pharmaceuticals, healthcare professionals and environmental services personnel routinely generate waste drugs which must be directed to one of several pre-defined waste streams. The output information of the pharmaceutical waste manager 10 is designed to be used at this immediate point of waste generation by these individuals who do not have the advanced chemical or regulatory training to make these waste stream judgments themselves. This is particularly significant because the pharmaceutical industry deals with many thousands of SKU's and the waste determination may vary by dosage form for a particular drug. Other industries typically deal with a much smaller number of bulk chemicals and the waste determination is typically done by technicians working for a hazardous waste broker or federally permitted treatment, storage and disposal facility (e.g., TSDF).

Figure 2:
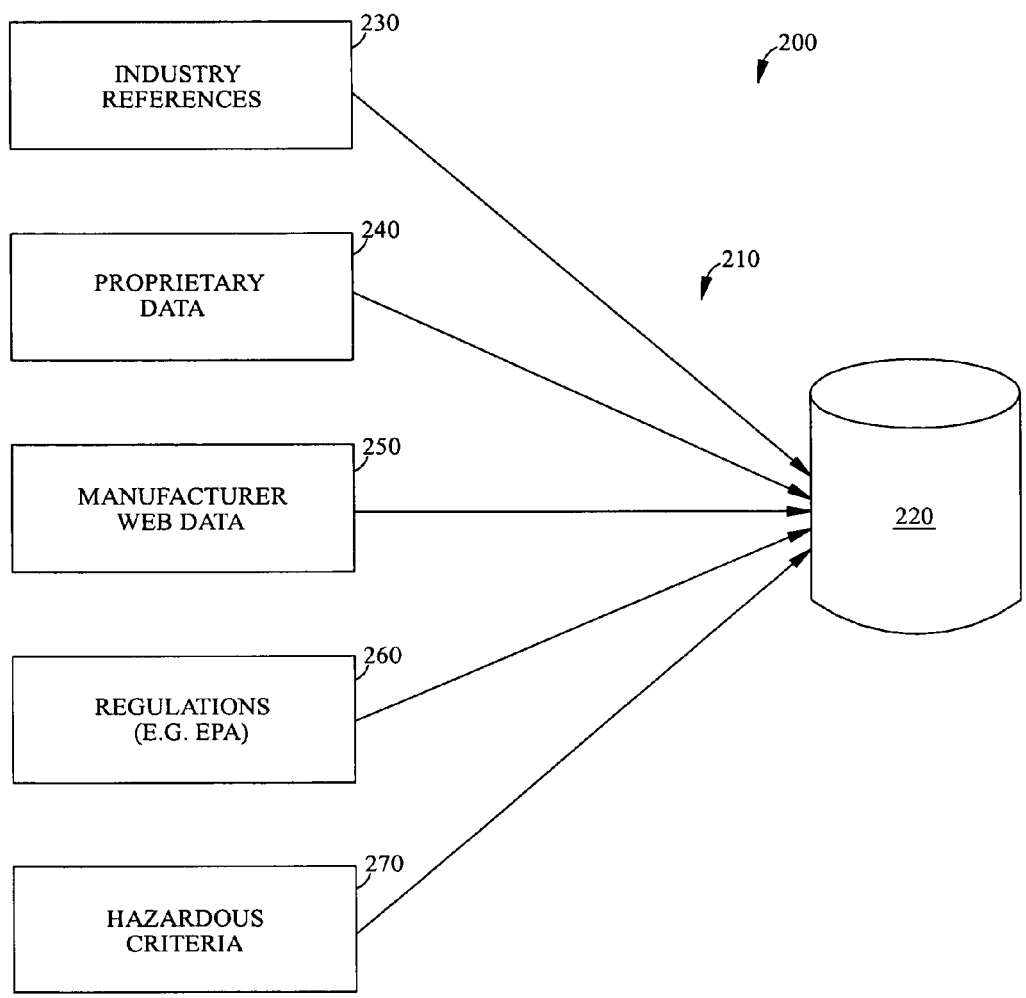
FIG. 2 is a general diagram of information included in the pharmaceutical waste manager of FIG. 1 in accordance with another exemplary embodiment.

FIG. 2 illustrates a general block diagram 200 of information included in pharmaceutical waste manager 10 (described with reference to FIG. 1), in accordance with another exemplary embodiment. As shown in diagram 200, data network 210 communicatively connects database 220 with industry references 230, proprietary data 240, manufacturer web data 250, EPA regulations 260, and hazardous criteria 270. References such as these provide database 220 with a collection of information such that subscribers to pharmaceutical waste manager 10 can look up a product by NDC (national drug code) number, partial NDC number, trade name, partial trade name, generic name, partial generic name, ingredient, or partial ingredient. If a name search is used, additional descriptive information is maintained by database 220 and can be provided for all products having that name, including the manufacturer and product strength.

The NDCs of pharmaceuticals are stored in database 220 as well as a summary of pharmaceuticals by product, by waste categorization, and by waste stream. As such, subscribers to pharmaceutical waste manager 10 can maintain a comprehensive list of pharmaceuticals which become hazardous waste when discarded. Advantageously, these relational associations of pharmaceuticals make it possible to have a formulary decision-making tool if multiple drug entities are therapeutically equivalent but one evidences a better waste disposal characteristic than the other.

Database 220 can also include waste designation information that can be related to or embedded in drug wholesalers' systems as to flag those items that become hazardous waste such that pharmacies can tag them with an appropriate label.

Figure 3:
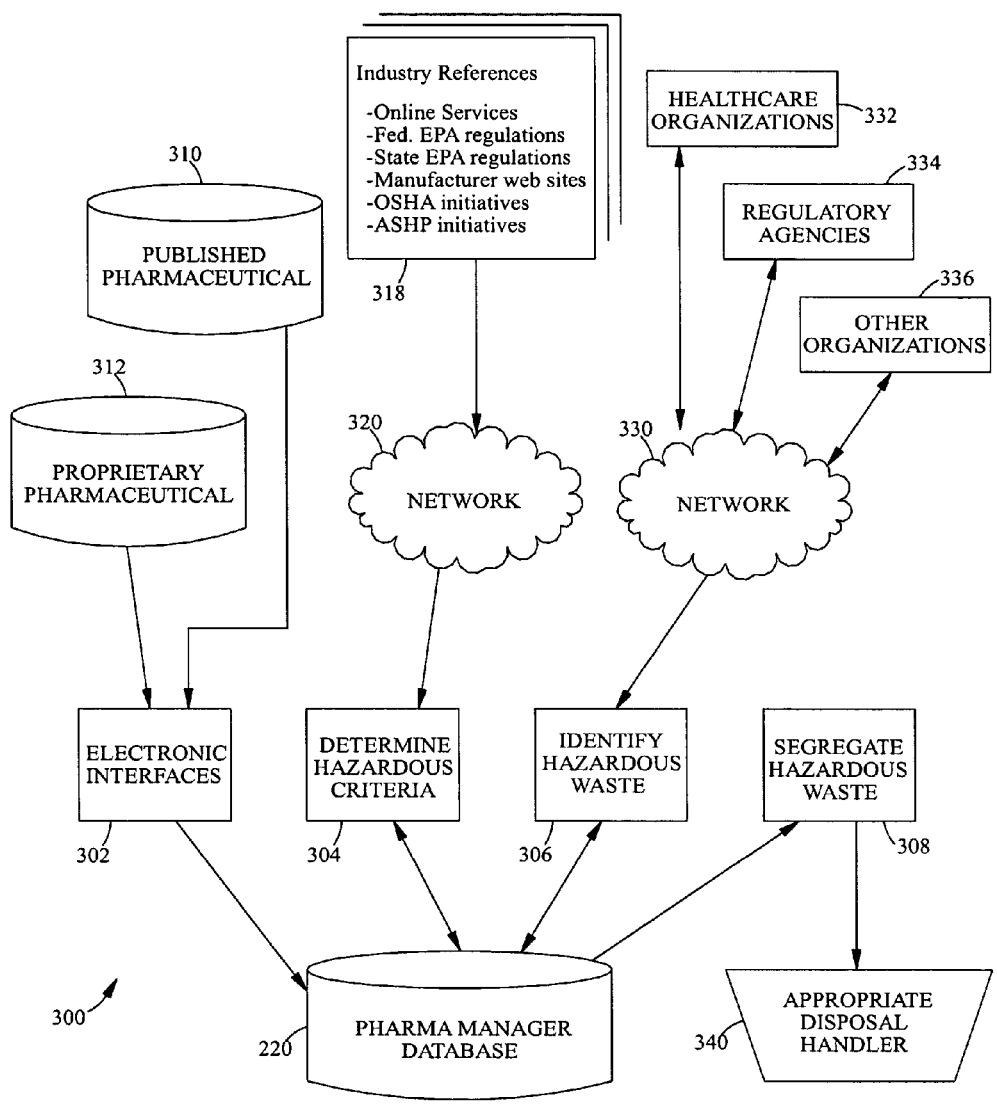
FIG. 3 is a diagram of a pharmaceutical hazardous waste system in accordance with another exemplary embodiment.

FIG. 3 illustrates a diagram 300 of a pharmaceutical hazardous waste system in accordance with another exemplary embodiment. As shown in diagram 300, database 220 has a communicative connection with electronic interfaces 302. Database 220 can be utilized to perform a hazardous criteria determination operation 304 and a hazardous waste identification operation 306. Further, database 220 can be used in a hazardous waste segregation operation 308.

Electronic interfaces 302 provide database 220 with access to published pharmaceutical information 310 and priority pharmaceutical information 312. As such, database 220 can obtain and store information relating to a wide range of pharmaceuticals from these sources. Additionally, database 220 can access industry references 318 via a network 320. Industry references 318 can include online services, federal EPA regulations, state EPA regulations, manufacture web sites, OSHA initiatives, ASHP initiatives, and other references. Using industry references 318 and pharmaceutical information contained in database 220, hazardous criteria can be determined in operation 304 and such criteria can be stored in database 220.

Health care organizations 332, regulatory agencies 334, and other organizations 336 can communicate via a network 330 to access database 220 and identify hazardous waste in operation 306. Network 330 can be the Internet, a private intranet, or any other type of network. Hazardous waste can be identified using hazardous waste criteria determined in operation 304 and other pharmaceutical information contained in database 220.

Once hazardous waste is identified, the hazardous waste can be segregated in operation 308. Segregation of hazardous waste can include basic segregations of toxic, ignitable, corrosive acid, corrosive base, and reactive, and can be customized to include the full range underlying the database. After segregation of hazardous waste, an appropriate disposal handler 340 is engaged. Heretofore, most of the items have been sent through medical waste disposal firms, in violation of RCRA. Using this system, either local or regional hazardous waste brokers manage the labeling, labpacking, manifesting, transporting, storage and disposal at a federally permitted RCRA facility, or national disposal firms provide this on-site service. Optionally, a very sophisticated waste generator can perform all services except transportation and disposal in-house.

Currently many healthcare organizations contract with hazardous waste disposal brokers or firms for laboratory waste, batteries and other known hazardous chemical waste. Advantageously, pharmaceutical waste manager 10 assists organizations in developing two ongoing waste streams (toxic and ignitable) and three occasional waste streams (corrosive-acid, corrosive-base and reactive). Additional ongoing waste streams can be included, such as non-hazardous pharmaceuticals waste into Regulated Medical Waste (RMW) incinerators or appropriately permitted municipal incinerators, trace chemotherapy waste into RMW incinerators; sewerable; and municipal solid waste (landfills).

Figure 4:
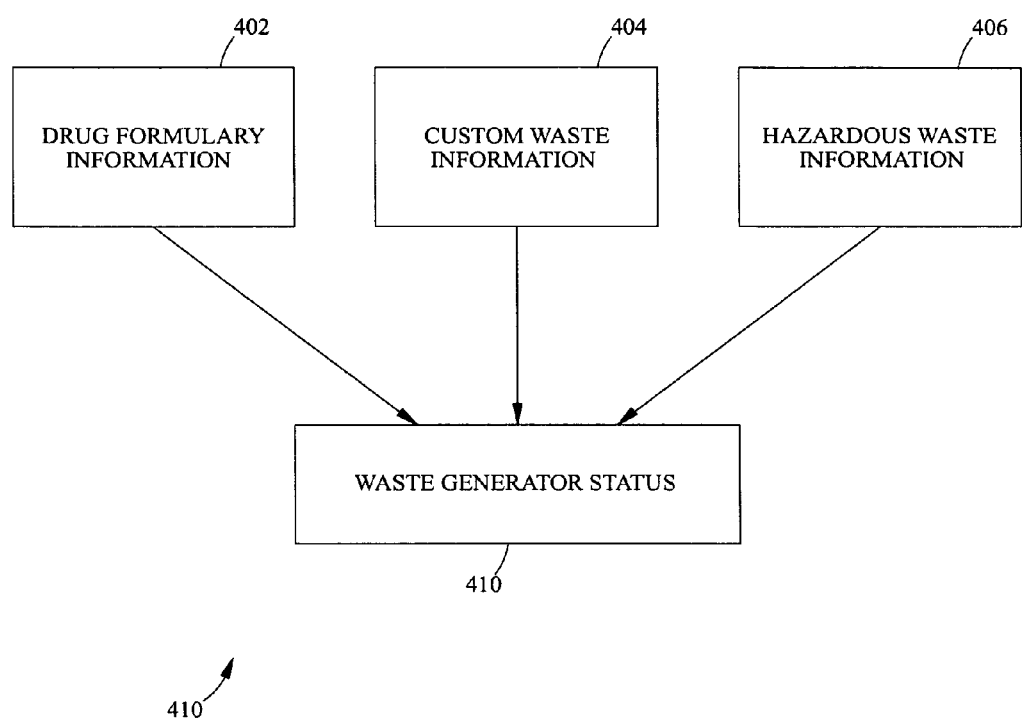
FIG. 4 is a general block diagram of a hazardous waste generator status system in accordance with another exemplary embodiment.

FIG. 4 illustrates a general block diagram 400 of a hazardous waste generator status system in accordance with another exemplary embodiment. As shown in diagram 400, drug formulary information 402, custom waste information 404, and hazardous waste information 406 are provided to establish a monthly waste generator status in an operation 410.

Every commercial entity that generates hazardous waste under RCRA must determine its generator status: large quantity, small quantity or conditionally exempt small quantity. Both large and small quantity generators must notify the U.S. EPA of their waste generation status and receive an Identification Number which resides with that physical site, henceforth, regardless of change of ownership or function. In this manner, the U.S. EPA is able to track potential environmental damage from owner to owner and function to function. Large quantity generators, which come under full regulation, must also prepare and have available a full emergency response plan, which includes notification of local area hospitals of their activities, provision of Material Safety Data Sheets (MSDS) and floor plans with indicated hazardous waste areas to local fire response units, notification of regional emergency response boards, and a two mile radius map indicating all streams, lakes, ponds, schools, hospitals and other public buildings, among other requirements.

Small quantity generators have lesser documentation requirements. Conditional exempt small quantity generators (CESQGs) do not need to notify the U.S. EPA but do need to identify and segregate hazardous waste and dispose of it in accordance with RCRA. CESQGs are allowed some leeway in a variety of areas so it is advantageous for an organization to be in this category. The generator should preferably be able to justify small or CESQG status by assuring that within a calendar month, they have not generated over 1 kg of P listed waste or over 100 Kg of total hazardous waste. A site also cannot accumulate more than certain amounts in total. In an exemplary embodiment, a customized real time tracking system coupled to or integrated into pharmaceutical waste manager 10 records weights of P list separate from U and D and provides monthly totals for P and total hazardous waste generation to document the current generator status.

Figure 5:
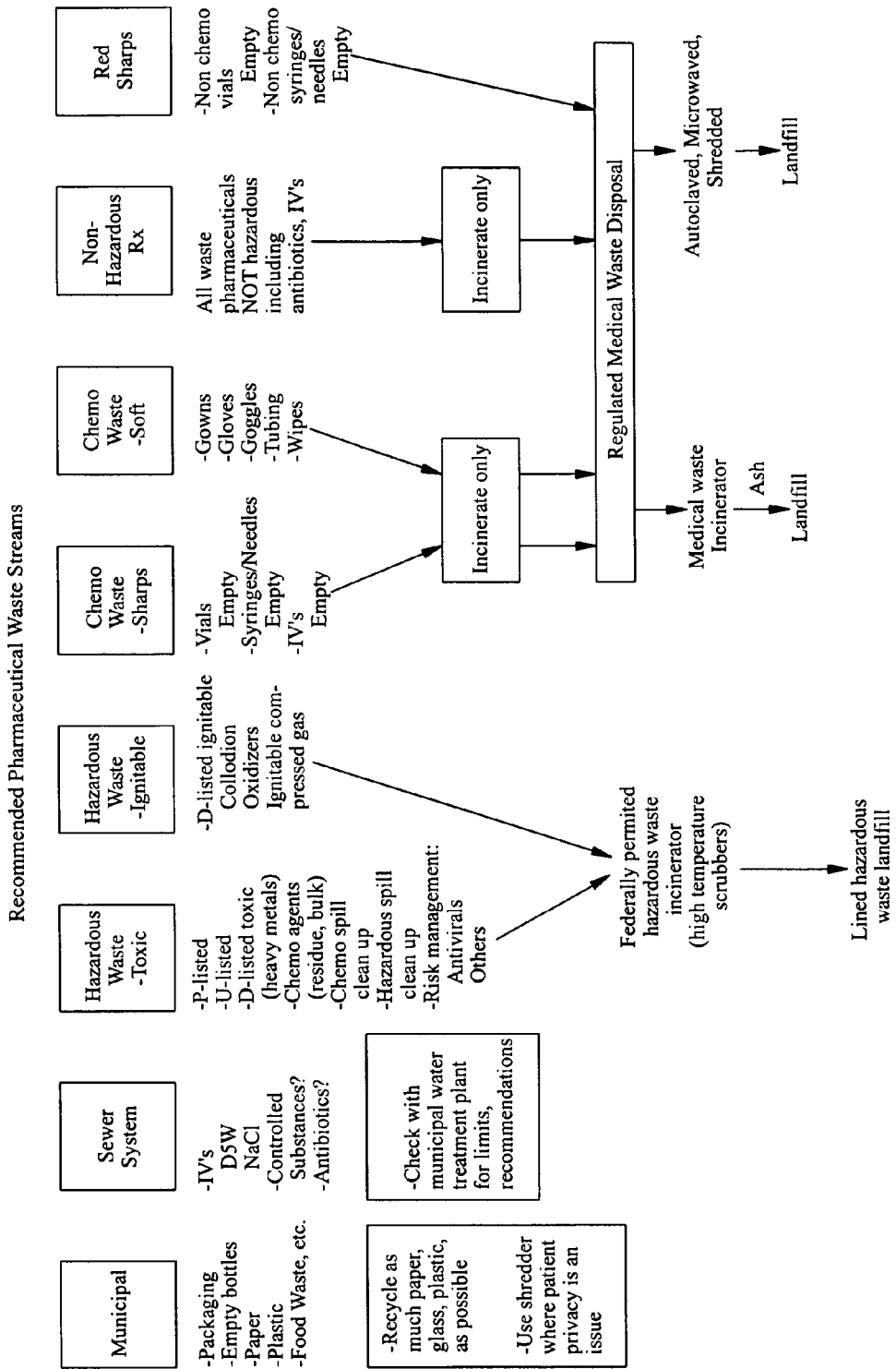
FIG. 5 is a block diagram of recommended pharmaceutical waste streams in accordance with another exemplary embodiment.

FIG. 5 is a block diagram of recommended pharmaceutical waste streams in accordance with another exemplary embodiment. As shown in the diagram, pharmaceutical waste streams can be routed to a variety of locations. For example, pharmaceutical waste streams can be disposed as municipal waste, in the sewer system, as toxic hazardous waste, as ignitable hazardous waste, as chemotherapy waste-sharps, as chemotherapy waste-soft, as non-hazardous waste, and as red sharps.

FIG. 5 illustrates an exemplary system for the disposition of pharmaceutical waste. While disposition as common municipal waste, garbage cans, dumpsters, etc. is to be avoided due to safety and diversion concerns, it does occur. Such disposition is specifically prohibited for RCRA hazardous waste. Similarly, a number of waste pharmaceuticals are disposed through sewering. While non-hazardous pharmaceuticals may in some cases be disposed of legally in this manner, based on the requirements of the local water treatment facility, RCRA hazardous wastes are specifically prohibited from such disposal.

A major source of inappropriate disposal of RCRA hazardous waste is chemotherapy containers, primarily sharps containers used for glass and needle disposal. Chemotherapy soft waste streams, using plastic bags, preferably contain trace amounts of drugs but they are sometimes used for unused IV bags containing RCRA hazardous waste. These chemotherapy waste containers are sent through regulated medical waste disposal facilities, and may be incinerated or simply microwave, autoclaved and landfilled. In either case, they are not being treated as RCRA hazardous waste and are therefore in violation of RCRA. This issue will become more severe if, and when, the federal government expands RCRA to properly categorize more chemotherapy as hazardous.

Even non-hazardous pharmaceutical waste is to be segregated and documented before being shipped to a regulated medical waste incinerator or municipal incinerator which may be able to legally dispose of this waste stream if so permitted. Finally, it is common for partial vials and other drugs to be placed into red infectious sharps containers, which violates both the regulated medical waste incinerator protocols, and if, hazardous waste, RCRA regulations.

Pharmaceutical waste manager 10 assists organizations in establishing and maintaining the proper hazardous waste segregation into primarily hazardous waste-toxic or hazardous waste-ignitable waste streams to be properly labeled, stored, manifested, shipped and disposed in accordance with RCRA. The less common waste streams of acids, bases and reactives can be managed as occasional lab-packs and do not constitute ongoing waste streams.

By way of example, any of the chemotherapy drugs that are listed as hazardous waste can be identified by pharmaceutical waste manager 10 as such when a subscriber looks up the drug. Search results can indicate that the drug is a P or U-listed federal hazardous waste, giving the appropriate P or U number. Further, the results can indicate the drug waste should be disposed of in the hazardous waste-toxic container. In addition, other chemotherapy agents are identified as "Risk Management" concerns and while not federally regulated, should be disposed of in the hazardous waste-toxic container. Those drug formulations that contain 24% or more alcohol are preferably identified as ignitable hazardous waste and instructions are to dispose of accordingly. By providing such instructions for the majority of pharmaceuticals in the marketplace, pharmaceutical waste manager can reduce hazardous pharmaceuticals from endangering human health or the environment.

Figure 6:
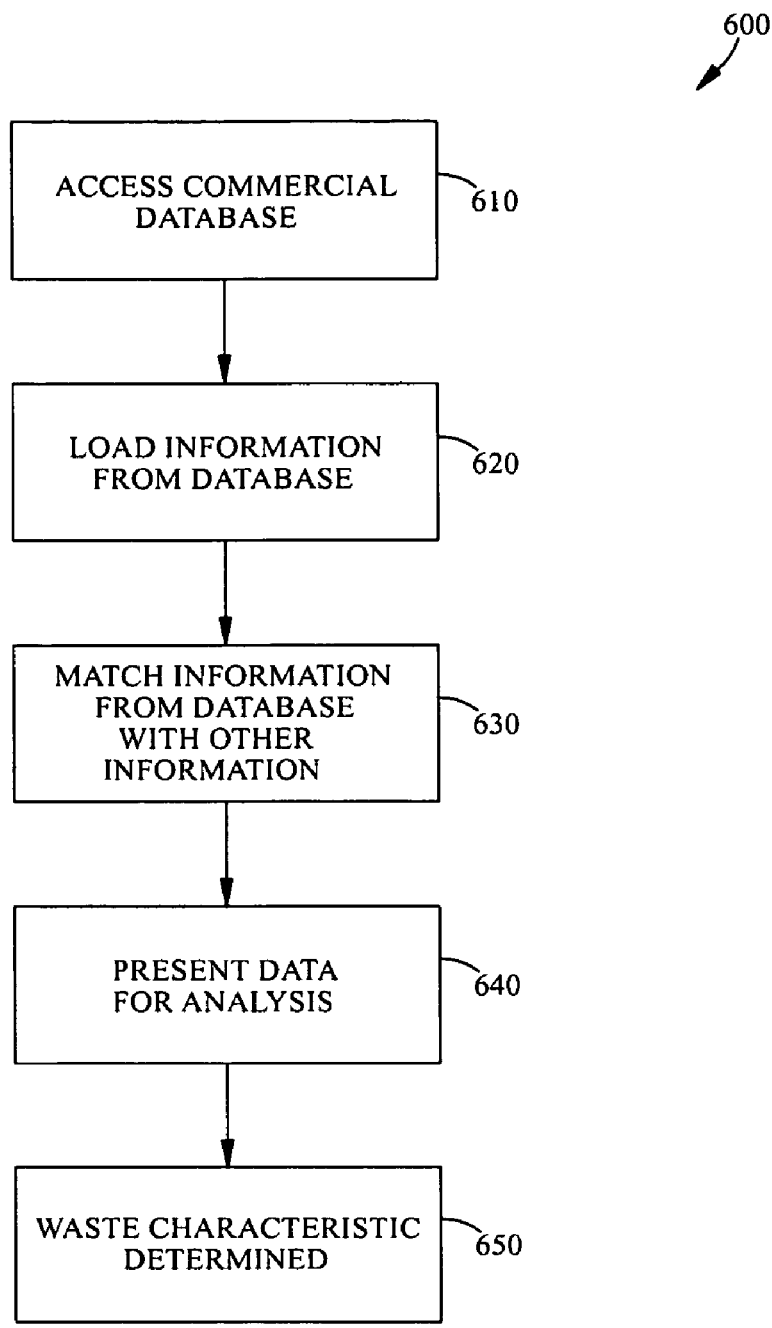
FIG. 6 is a flow diagram of an exemplary process for identification and management of hazardous waste information.

FIG. 6 illustrates a diagram 600 of exemplary operations performed in the process of bringing together pharmaceutical hazardous waste information, analysis, and presentation. These operations described are by way of example only. Additional operations or fewer operations can be performed. Furthermore, these operations can be wholly-computer enabled or computer enabled with the assistance of a human analyst.

In an operation 610, pharmaceutical waste manger 10 accesses a commercial database. As described with reference to FIG. 1, a commercial database can be the Medispan Database. Access to the commercial database can be made through a network, such as, the Internet, an Intranet, or any other communicative network. In an operation 620, pharmaceutical waste manager 10 loads information from the commercial database accessed in operation 610.

In an operation 630, pharmaceutical waste manager 10 matches information from the commercial database with other information. Other information may be obtained from historical information already contained in the database of pharmaceutical waste manager 10 or information available from other sources coupled to pharmaceutical waste manager 10 via a network. Once information is matched from the database, an operation 640 is performed in which data is presented for analysis. Data can be presented in a variety of different ways. For example, data can be presented by storage in data structures within a database or displayed on a computer screen for the review of the human analyst or both. Once the data on pharmaceutical hazardous waste is presented for analysis, an operation 650 is performed in which waste characteristics are determined. Waste characteristics can be determined in a variety of ways. For example, artificial intelligence algorithms can be employed to make determinations based on database information both stored and collected. Further, waste characteristic information can be determined using intelligence provided by one or more human analysts.

Once waste characteristics are determined, the characteristic information is stored in the database and made accessible to a client via a network. For example, a client can access waste characteristic data via the Internet by clicking a hypermedia link on a web site for a health care facility. By way of another example, a client may access waste characteristic information by clicking on a hypermedia link from a medical information web site. A wide range of access means can be employed.

Advantageously, the systems and methods described with reference to FIGS. 1-6 make it possible to assist with the calculations needed to determine if a drug pre-approval requires an environmental assessment as part of its FDA application, especially if other drugs of like mode of action are considered.

FIGS. 7, 8, and 9 are exemplary displays of graphical user interfaces used in the presentation of information from pharmaceutical waste manager 10. The user interfaces shown in the FIGURES can be accessed once the user, organization, and jurisdiction are identified. Authorized users can be identified by his or her e-mail address, for example. As described previously, an organization can be a subscriber to pharmaceutical waste manager 10 and the organization can authorize one or more individuals to access manager 10. Preferably, whenever a user selects a product, he or she preferably indicates that the analysis should be for a specific country and state or province.

Using the graphical user interfaces of FIGS. 7, 8, and 9, someone using pharmaceutical waste manager 10 can select a product to review through several different ways. For example, he or she can specify a specific product identified by the NDC code. While full NDC codes are of the form NNNNN-NNNN-NN, the system preferably allows someone to omit leading zeroes from each portion of the code. A product can also be identified by the Universal Product Code otherwise known as the UPC code. Products can also be identified by partial NDC codes of the form NNNNN-NNNN. If the operator specifies a partial NDC code, the system preferably presents a list of all NDC codes within that range and allows the operator to select a particular NDC.

Products can also be reviewed using a full or partial product theme, such as a particular brand name or a less specific generic name. If the operator enters a partial product name, the system preferably presents a list of full product names and allows the operator to select a specific product name. The system presents a list of NDCs within that product name and allows the operator to select a particular NDC.

A product can also be identified from a full or partial ingredient name. If the operator enters a partial ingredient name, the system preferably allows the operator to select from a list of full ingredient names. The system displays a list of all products which include that ingredient name and allows the operator to select a particular product. When an operator enters a product name or ingredient name, he or she can restrict the selection of products of a particular strength or those from a particular manufacturer.

An exemplary user interface should include the following information to properly identify a particular product. Information can include the full NDC code, formatted per the manufacturer's specification; the product name, brand name, or generic name; the drug name; the manufacturer; the product strength; the package size and form; an indication if the product is prescription or over the counter; and an indication if the product is a DEA (Drug Enforcement Administration) controlled substance.

Figure 10:
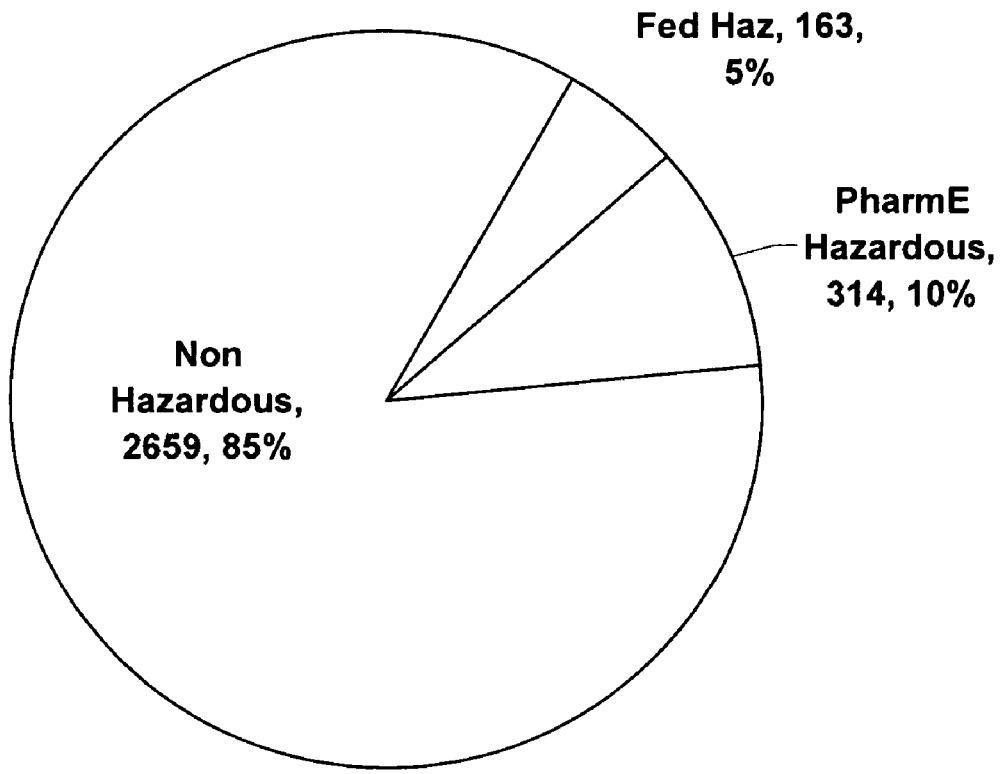
FIG. 10 is a pie chart depicting a summary of example results from a formulary analysis by the pharmaceutical waste manager of FIG. 1.

FIG. 10 illustrates a pie chart summarizing results from a formulary analysis of an example institution, such as a hospital. The example pie chart graphically depicts the breakdown of non-hazardous samples, federally hazardous samples, and samples that are noted as hazardous by the pharmaceutical waste manager. The results depict a summary from more detailed data contained in a spreadsheet.

FIG. 11 illustrates a spreadsheet including detailed information regarding pharmaceuticals from an exemplary formulary analysis. The detail can include the NDC number for the pharmaceutical, a label name for the pharmaceutical NDC report, a waste classification for the pharmaceutical, a waste stream for the pharmaceutical, an EPA code for the pharmaceutical, and a reason for the pharmaceutical classification. Additional, fewer, or different categories may be included in a formulary analysis.

The user interface display preferably includes the following information when the system displays waste characteristics for a particular product. Example information can include (1) product identifying information; (2) a summary, color-coded result, indicating the particular product becomes federally hazardous waste, state hazardous waste, recommended treatment as risk management hazardous waste, or is non-hazardous; (3) a message indicating that a particular state may have more stringent criteria than the federal government; (4) a waste stream determination, customized to the particular operation requirements of the organization; (5) the federal EPA code or codes associated with a particular waste; (6) additional support in detail about the determination, including the reason code, concentration calculations, reference sources, ingredient list, and other criteria; and (7) the date and time of the particular query.

In an exemplary embodiment, pharmaceutical waste manager 10 includes a login system in which all queries are logged to create an audit trail of the action.

While the exemplary embodiments illustrated in the figures and described above are presently preferred, it should be understood that these embodiments are offered by way of example only. Other embodiments may include, for example, a wide variety of ways to convey pharmaceutical hazardous waste information, such as, wireless application protocol (WAP), personal digital assistant (PDA) protocols, and other presentation means. Further, while exemplary embodiments describe the invention in the context of RCRA and EPA requirements, the invention may extend to other waste requirements. The invention is not limited to a particular embodiment, but extends to various modifications, combinations, and permutations that nevertheless fall within the scope and spirit of the appended claims.

What is claimed is:

1. A computer program application embodied in a computer readable medium and configured for use in a medical dispensing software program to generate proper labels and disposal recommendations for pharmaceuticals, the application comprising:

pharmaceutical waste information associated with a pharmaceutical, the pharmaceutical waste information being gathered from a plurality of sources, wherein the pharmaceutical waste information includes information regarding finished pharmaceutical dosage forms of the pharmaceutical, the pharmaceutical waste information including analysis and notes from one or more reviewers of the pharmaceutical; and a user interface that presents the information associated with the pharmaceutical waste information to a client, wherein the client enters a pharmaceutical name and is provided with a pharmaceutical waste disposal recommendation.

2. The program application of claim 1, wherein the pharmaceutical waste disposal recommendation comprises a disposal recommendation for an empty container previously containing the pharmaceutical.

3. The program application of claim 1, wherein the pharmaceutical waste disposal recommendation comprises a labeling recommendation for a primary container of the pharmaceutical.

4. The program application of claim 1 wherein the recommendation is presented in a different color depending on a severity level.

5. The program application of claim 4, wherein a red color represents a high severity of hazardous waste.

6. The program application of claim 1, wherein the pharmaceutical waste disposal recommendation includes information on an appropriate waste disposal system.

7. The program application of claim 1, further comprising benchmarking information having data regarding a formulary of the pharmaceutical and demographic data.

8. The program application of claim 7, wherein the benchmarking information comprises usage and cost information.

9. The program application of claim 1, further comprising a link to a supporting Material Safety Data Sheet accessible via the Internet.

10. A method of providing disposal recommendations for pharmaceuticals, the method comprising:
using a first processing system to maintain a pharmaceutical waste information processing unit that receives and processes requests for pharmaceutical waste information including data from reviewers and information regarding finished dosage forms;
receiving a signal for invoking the pharmaceutical waste information processing unit from a remote processing system via a network wherein the signal is transmitted when a client enters a pharmaceutical name; and
providing a recommendation in response to the signal, wherein the recommendation includes any one of the labeling recommendation for a primary container of the pharmaceutical, a disposal recommendation for an empty primary container of the pharmaceutical, and a disposal recommendation for the pharmaceutical.

11. The method of claim 10, wherein the pharmaceutical waste information date comprises non-hazardous information which is differentiated into sewerable, municipal solid waste, and incinerable.

12. The method of claim 10, wherein the response to the signal is provided via a hand-held bar code scanner that provides the disposal recommendation using an electronic display.

13. The method of claim 10, further comprising printing a label for the primary container based on the labeling recommendation.

14. The method of claim 10, wherein the labeling recommendation comprises Department of Transportation (DOT) guidance.

15. A device configured to receive pharmaceutical information and provide a disposal recommendation in response to the received pharmaceutical information, the device comprising:
an input component configured to receive a pharmaceutical identifier;
a memory containing programmed instructions that determines a pharmaceutical based on the pharmaceutical identifier and that provides a disposal recommendation based on stored information associated with the pharmaceutical; and
an output component that presents the disposal recommendation, wherein the output component communicates the disposal recommendation to a computer application associated with a health care medical dispensing program.

16. The device of claim 15, wherein the input component comprises a bar-code scanner.

17. The device of claim 15, wherein the output component comprises an electronic display.

18. The device of claim 15, wherein the output component comprises a label printer configured to print labels for containers of the pharmaceutical.

19. The device of claim 15, wherein the output component further provides instructions for a unit dose packaging software to mark the pharmaceutical according to the disposal recommendation.

20. The device of claim 15, wherein the input component comprises an Internet-based application communicatively coupled to the Internet.

* * * * *